(12) United States Patent
Thorogood et al.

(10) Patent No.: US 9,039,995 B2
(45) Date of Patent: May 26, 2015

(54) SELF-METERING SYSTEM AND TESTING DEVICE WITH CASING AND SLIDING MEMBER TO CUT-OFF AND SET SAMPLE VOLUME

(75) Inventors: Stephen Daniel Thorogood, Etobicoke (CA); Paul Saunders, Christiansted, VI (US)

(73) Assignee: Cardiogenics Inc., Mississauga (CA)

( * ) Notice: Subject to any disclaimer, the term of this patent is extended or adjusted under 35 U.S.C. 154(b) by 291 days.

(21) Appl. No.: 13/555,002

(22) Filed: Jul. 20, 2012

(65) Prior Publication Data

US 2013/0183768 A1 Jul. 18, 2013

Related U.S. Application Data

(63) Continuation of application No. PCT/CA2011/050043, filed on Jan. 25, 2011.

(60) Provisional application No. 61/298,148, filed on Jan. 25, 2010.

(51) Int. Cl.
*B01L 3/00* (2006.01)
*G01N 21/78* (2006.01)

(52) U.S. Cl.
CPC .............. *G01N 21/78* (2013.01); *B01L 3/502* (2013.01); *B01L 3/508* (2013.01); *B01L 2200/0605* (2013.01); *B01L 2200/141* (2013.01); *B01L 2300/045* (2013.01)

(58) Field of Classification Search
None
See application file for complete search history.

(56) References Cited

U.S. PATENT DOCUMENTS

| 5,651,401 A * | 7/1997 | Cados ........................... 141/129 |
| 6,269,704 B1 | 8/2001 | Ziv et al. |
| 2004/0156746 A1 | 8/2004 | Larsen |

FOREIGN PATENT DOCUMENTS

CA  2555621 A1  2/2007

* cited by examiner

*Primary Examiner* — Robert Xu
(74) *Attorney, Agent, or Firm* — Bret E. Field; Bozicevic, Field & Francis LLP

(57) ABSTRACT

A testing cartridge for metering of a sample to be tested. The testing cartridge includes a casing defining a casing opening and a sliding member defining a sliding member opening. The casing opening or the sliding member opening can define a specified volume, wherein the casing opening and the sliding member opening collectively define a sample application region dimensioned to accommodate receiving an amount of sample exceeding the specified volume. The sliding member is movable transversely to the casing opening by having the sliding member and the casing traverse across each other's respective openings to remove excess sample from the received amount of sample and retain the specified volume from the received amount of sample.

9 Claims, 18 Drawing Sheets

SELF-METERING SYSTEM AND TESTING DEVICE WITH CASING AND SLIDING MEMBER TO CUT-OFF AND SET SAMPLE VOLUME

CROSS-REFERENCE TO RELATED APPLICATIONS

This application is a continuation of PCT Application Serial No. PCT/CA2011/040043 filed on Jan. 25, 2011; which application claims the benefit of priority of U.S. Provisional Application No. 61/298,148 filed Jan. 25, 2010, the contents of which applications are herein incorporated by reference.

FIELD

Example embodiments described herein relate generally to testing devices for receiving of samples which contain analytes to be tested.

BACKGROUND

Current hospital and clinical laboratories are furnished with highly sophisticated and automated systems which have capabilities to run up to several thousand samples per day. These high throughput systems have automatic robotic arms, pumps, tubes, reservoirs, and conveying belts to sequentially move tubes to proper position, deliver the reagents from reservoirs, perform mixing, pump out the solutions to waste bottles, and transport the tubes on a conveyer to various modules.

Such complicated and high costs systems are generally not desired, and may not be readily adapted for short-run or individual testing procedures.

Immunoassays are important analytical systems used today in clinical laboratories. Existing Point-of-Care (POC) immunoassay devices utilize a wide variety of techniques for sample analysis. The drive towards immunoassay POC technology has produced several rapid immunoassay devices that yield results at a doctor's office or clinic within minutes. Examples of conventional POC immunoassay devices include relatively simplistic designs such as dip-sticks and test strips using relatively inexpensive support mediums that are easily operated by health practitioners as well as lay people.

In order to deliver a consistent sample volume to a reaction chamber or region of an immunoassay device, conventional designs have employed various principles for controlling the dynamic fluid movements, which may rely on several principles utilized either individually or in combination. These include controlled fluid movements in channels and capillaries which typically need to be designed for the specific fluid. It may be unsuitably complex to manufacture systems with such channels and capillaries to within specific tolerances, typically at the micron or submillimeter order of magnitude. For example, in such systems, liquids are transported by means of capillary forces which in turn makes high demands on the accuracy and form of the capillary channels and consequently results in correspondingly expensive and complex manufacturing processes. Additional fluid properties may also need to be specifically addressed in such systems, such as viscosity, etc.

Complex mechanisms which generate external forces have also been employed in some conventional testing devices to deliver consistently measured volumes to the reaction chambers in order to facilitate fluid migration and movements. There are conventional devices that have employed vacuum, centrifugal forces, positive pressure or relying on internal fluid forces. These forces include pressure in a negative (vacuum) or in a positive form. Also, mechanisms for generating centrifugal forces have been employed to control fluid volumes, as well as the use of electroosmotic forces.

Such systems may be relatively complex, which may not be suitable for many POC applications. For example, liquid transport by externally applied forces such as by centrifugation, rotation or by pumping generally require additional costly apparatuses such as centrifuges or pumps. In addition, these systems may often require additional process steps which usually have to be carried out outside of the device because such microfluidic devices can often only be equipped with dry chemistry reagents for manufacturing and stability reasons.

SUMMARY

Example embodiments relate to a Point-of-Care (POC) testing device which enables the delivery of a consistent measured volume(s) in a testing device testing cartridge. An actuation mechanism is also provided for effecting metering of the desired volume of the sample to the testing device.

In an example embodiment, there is provided a testing device which includes a testing cartridge having a casing defining a casing opening and a sliding member defining a sliding member opening. The casing opening or the sliding member opening can define a specified volume, wherein the casing opening and the sliding member opening collectively define a sample application region dimensioned to accommodate receiving an amount of sample exceeding the specified volume. The sliding member is movable transversely to the casing opening by having the sliding member and the casing traverse across each other's respective openings to remove excess sample from the received amount of sample and retain the specified volume from the received amount of sample.

In another example embodiment, there is provided a method for metering a sample. The method includes receiving an amount of sample in a sample application region, the sample application region being defined by a sliding member opening of a sliding member and a casing opening of a casing and at least one of the openings defining a specified volume, the received amount of the sample exceeding the specified volume; and moving the sliding member transversely to the casing opening by having the sliding member and the casing traverse across each other's respective openings to remove excess sample from the received amount of sample and retain the specified volume from the received amount of sample.

BRIEF DESCRIPTION OF THE FIGURES

Embodiments will now be described by way of example with reference to the accompanying drawings, in which like reference numerals are used to indicate similar features, and in which.

DETAILED DESCRIPTION OF EXAMPLE EMBODIMENTS

Figure 1A:
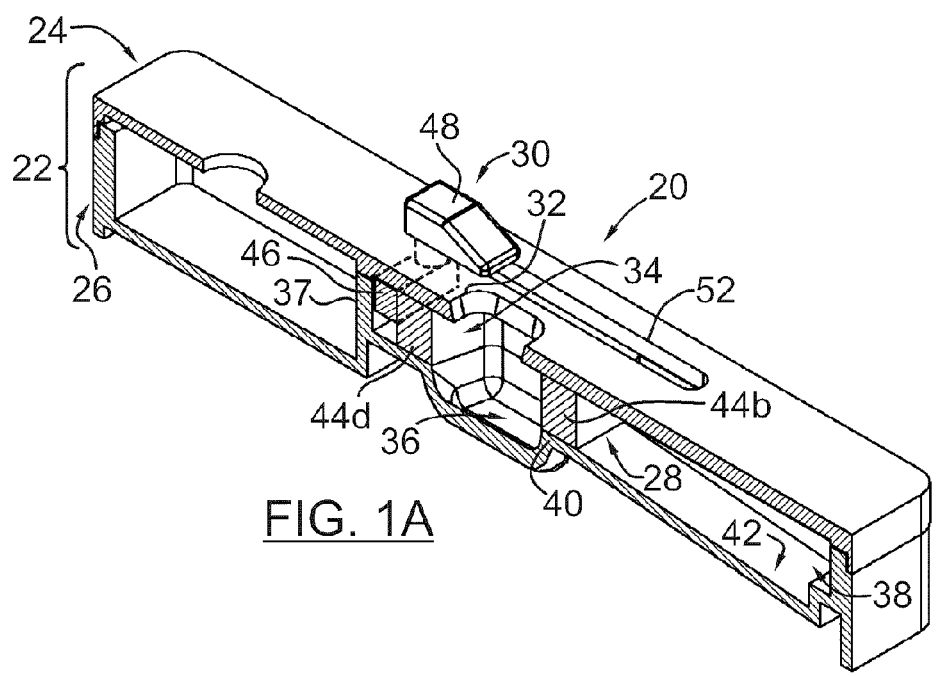
FIG. 1A shows a perspective sectional view of an example testing cartridge in accordance with a first example embodiment, wherein a casing defines an amount of sample to be tested.
Figure 1B:
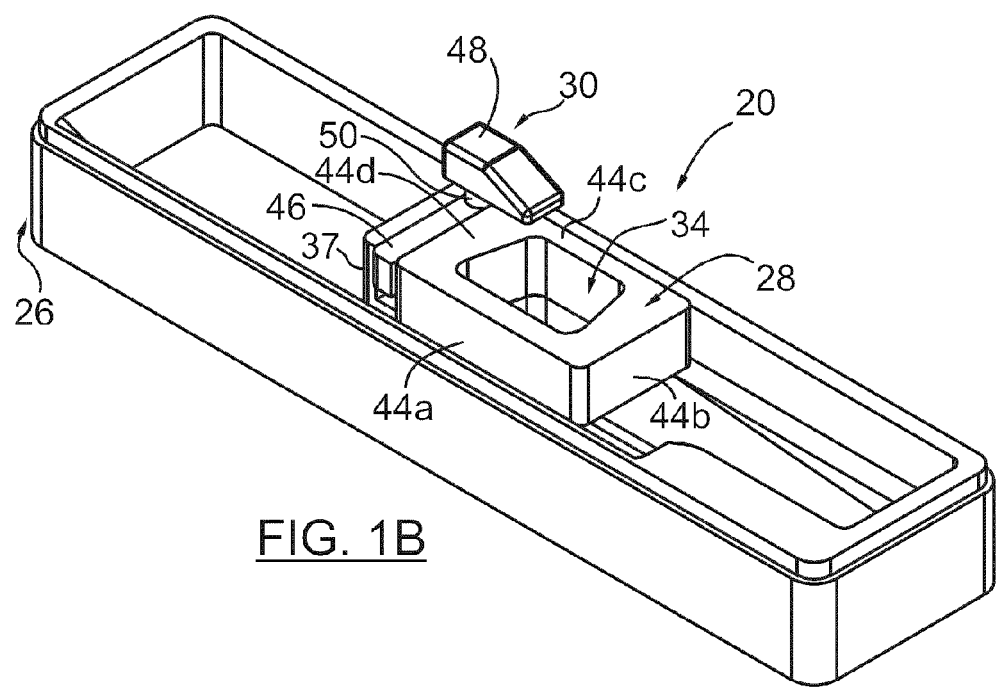
FIG. 1B shows a perspective view of the testing cartridge of FIG. 1A, shown without a top cover.

In accordance with an example embodiment, there is provided a testing device for metering of a sample, including a casing defining a casing opening; and a sliding member defining a sliding member opening, the casing opening or the sliding member opening defining a specified volume, the casing opening and the sliding member opening collectively defining a sample application region dimensioned to accommodate receiving an amount of sample exceeding the specified volume, wherein the sliding member is movable transversely to the casing opening by having the sliding member and the casing traverse across each other's respective openings to remove excess sample from the received amount of sample and retain the specified volume from the received amount of sample.

In accordance with another example embodiment, the testing device may further include an actuation mechanism, the actuation mechanism including an engaging member for engaging the sliding member for the transverse movement of the sliding member and a receiving member for receiving an actuation force for movement of the actuation mechanism, thereby moving the sliding member.

In accordance with another example embodiment, there is provided a method for metering a sample. The method includes receiving an amount of sample in a sample application region, the sample application region being defined by a sliding member opening of a sliding member and a casing opening of a casing and at least one of the openings defining a specified volume, the received amount of the sample exceeding the specified volume; and moving the sliding member transversely to the casing opening by having the sliding member and the casing traverse across each other's respective openings to remove excess sample from the received amount of sample and retain the specified volume from the received amount of sample.

In accordance with yet another example embodiment, there is provided a testing system, including: a testing cartridge including a casing defining a casing opening, and a sliding member defining a sliding member opening, the casing opening or the sliding member opening defining a specified volume, the casing opening and the sliding member opening collectively defining a sample application region dimensioned to accommodate receiving an amount of sample exceeding the specified volume, wherein the sliding member is movable transversely to the casing opening by having the sliding member and the casing traverse across each other's respective openings to remove excess sample from the received amount of sample and retain the specified volume from the received amount of sample; a receiving interface for receiving of the testing cartridge; and an actuation member in the receiving interface for engaging the receiving member of the actuation mechanism for moving of the sliding member.

It can be advantageous to make diagnostic assays faster, cheaper and simpler to perform while maintaining precision and reliability, which has lead to the progression of point of care (POC) test products. POC products have allowed for the measurement of analytes from samples, in a relatively simple and cost effective detection for a myriad of analytes for assisting in patient management. POC testing is attractive as it rapidly delivers results and enables faster clinical management which leads to improved patient outcomes. Examples of POC tests include blood chemistry such as glucose, lactate, electrolytes, as well as hematology, immunodiagnostics, drugs of abuse, serum cholesterol, fecal occult blood test ("FOBT"), pregnancy, and ovulation.

While there are many permutations to the design of the disposable cartridges employed in various POC test products, an element of their design is to provide accurate testing results. In order to provide accurate testing results, it is advantageous to have consistency measured testing volumes of the sample to be tested. Immunoassay procedures performed in laboratories or using POC devices require an accurate sample volume to deliver reliable results.

There are some developments in individual assays which may be carried out by non-technical personnel at such sites as doctor's offices, clinics, the home, rest homes, and the like. In order to ensure that non-technical individuals may accurately perform these tests, it is advantageous to implement procedures which are relatively simple and that there be few, if any, measurements to be made by the individual. For this purpose, it would be advantageous to have a device which can be used individually for each assay determination without the requirement of technical training.

Example embodiments relate to a POC testing device or testing cartridge which provides the measurement of a consistently measured volume(s) of sample to a reaction region of a testing cartridge.

Reference is now made to FIGS. 1A to 1G, which show an example POC testing cartridge 20 for metering of a sample containing analytes to be tested, in accordance with an example embodiment. In the embodiment shown, the testing cartridge 20 generally includes a casing 22 which defines an amount of sample to be tested. The casing 22 includes a top cover 24 and a bottom cover 26 which connect together to collectively generally house the testing cartridge 20. As shown, the testing cartridge 20 also includes a sliding member 28 and an actuation mechanism 30 for moving of the sliding member 28 in a transverse direction.

Figure 1C:
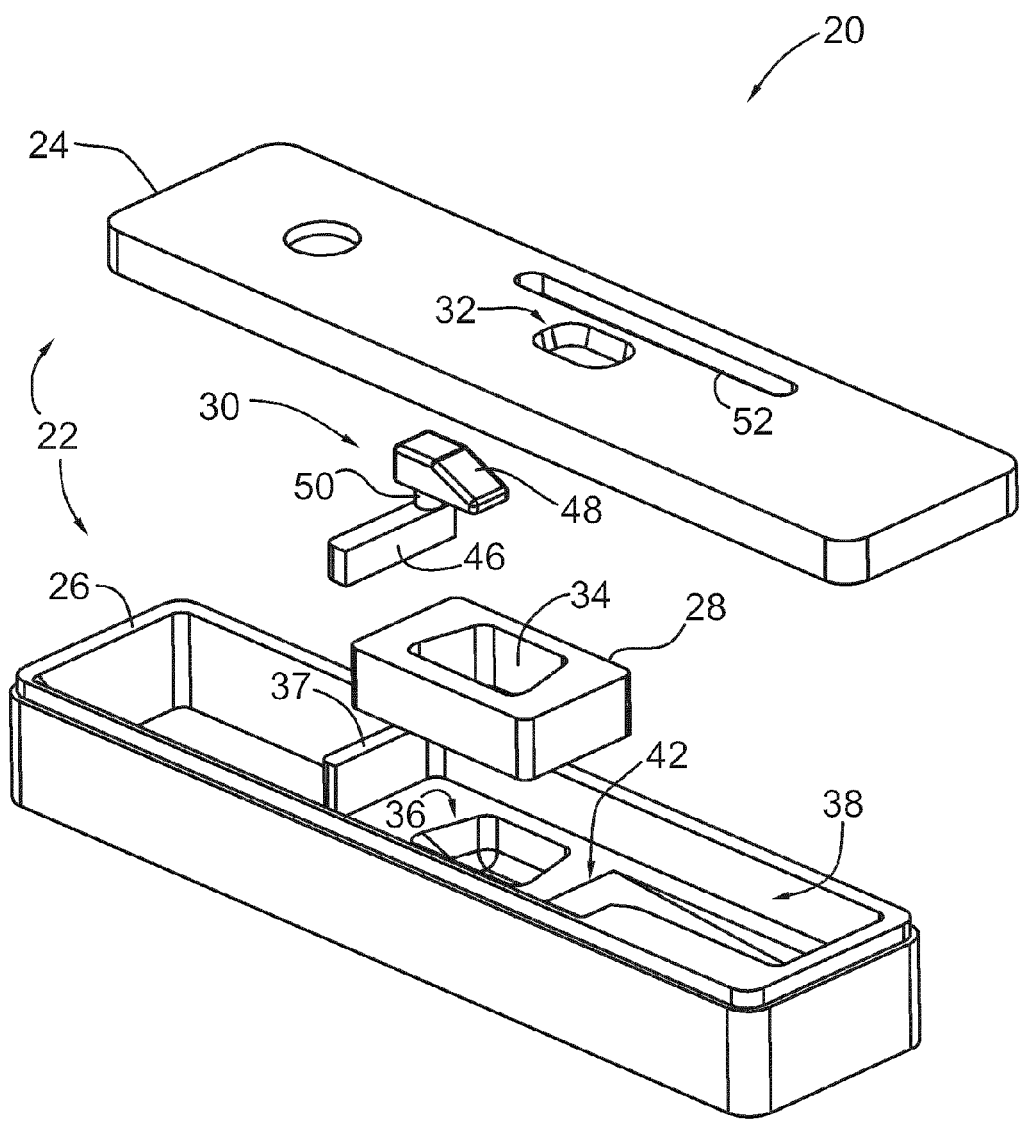
FIG. 1C shows an exploded perspective view of the testing cartridge of FIG. 1A.
Figure 1D:
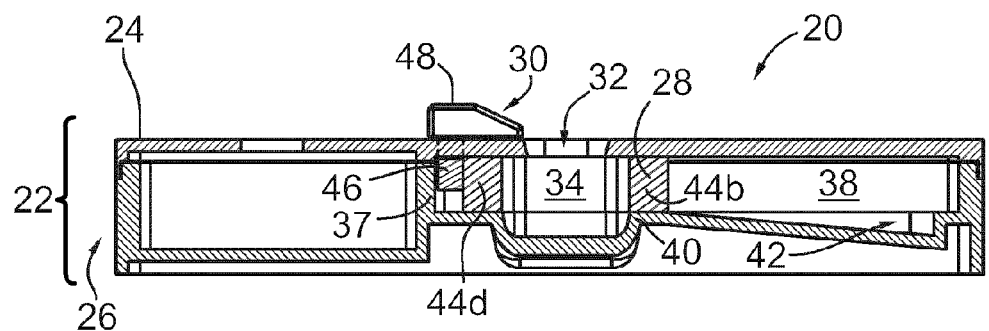
FIG. 1D shows a side sectional view of the testing cartridge of FIG. 1A.
Figure 1E:
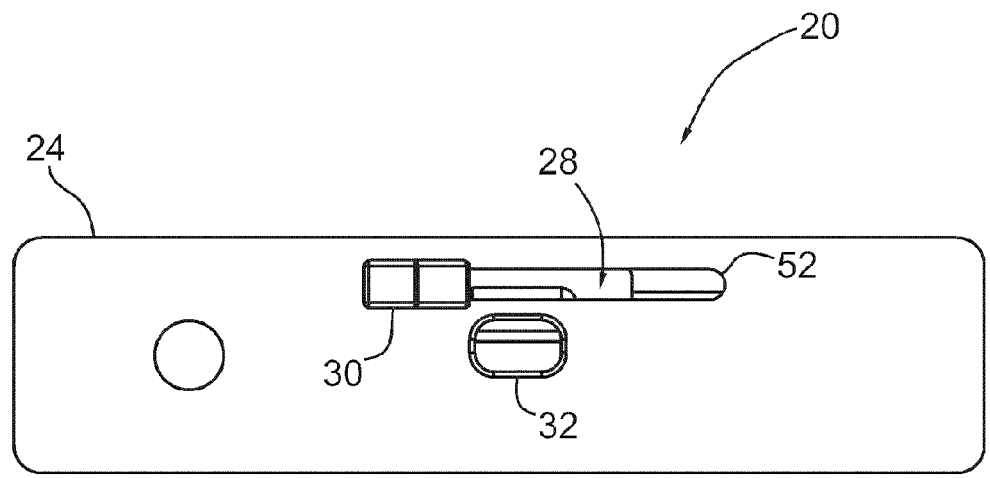
FIG. 1E shows a top view of the testing cartridge of FIG. 1A.
Figure 1F:
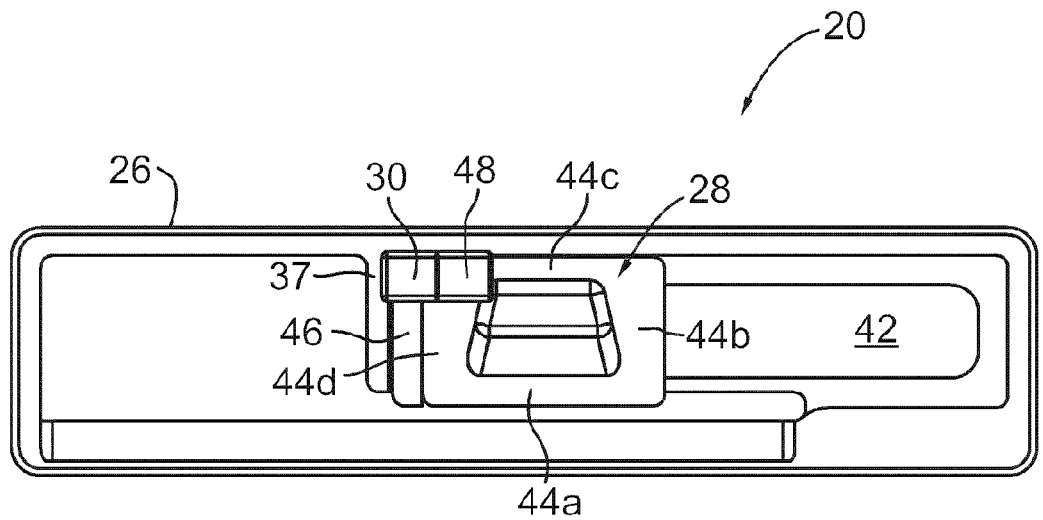
FIG. 1F shows a top view of the testing cartridge of FIG. 1A, shown without the top cover.
Figure 1G:
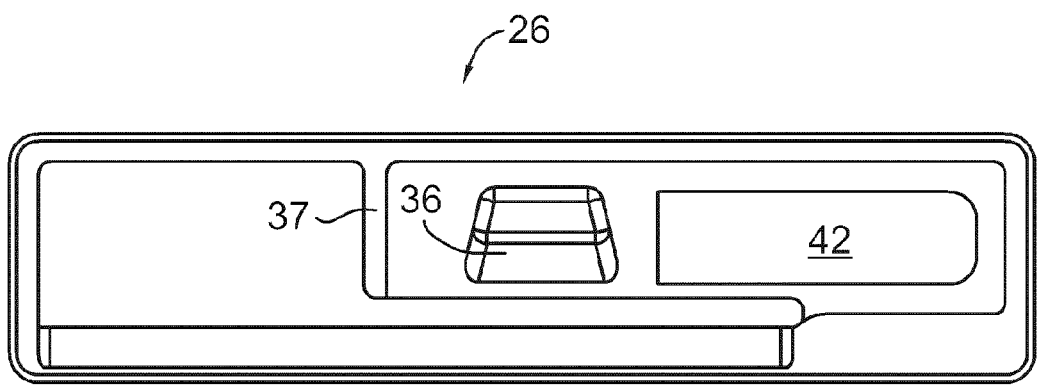
FIG. 1G shows a top view of a bottom cover of the testing cartridge of FIG. 1A.
Figure 2:
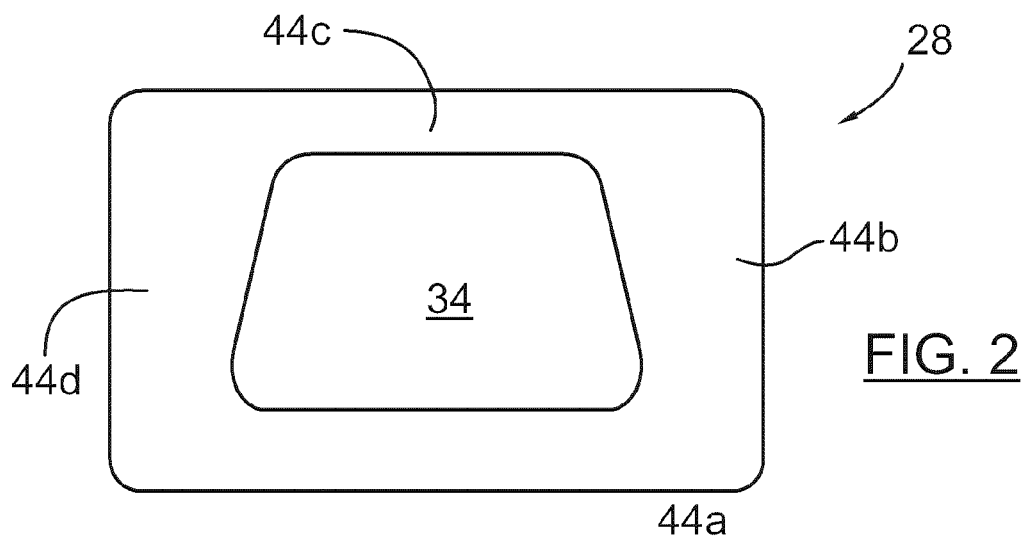
FIG. 2 shows a top view of an example sliding member in accordance with an example embodiment, to be used in the testing cartridge of FIG. 1A.

Referring still to FIGS. 1A to 1G, a sample receiving region may be defined by a port 32, a sliding member opening 34, and a casing opening 36. For example, a sample to be tested can be applied to the sample receiving region, which can be metered by the cartridge 20 to provide consistently measured volumes in accordance with example embodiments. The port 32 is defined by the top cover 24, and the casing opening 36 is defined by the bottom cover 26. Referring briefly to FIG. 2, which shows a top view of the sliding member 28, the sliding member opening 34 is defined by four enclosed sidewalls 44a-44d of the sliding member 28. In the example shown in FIGS. 1A to 1G, the casing opening 36 defines a specified volume, which is the desired volume of the sample to be tested. In use, the sample receiving region is dimensioned to accommodate an amount of sample which exceeds the specified volume defined by the casing opening 36, wherein the sample may fill at least part of the sliding member opening 34 as well. Although the sliding member opening 34 and casing opening 36 are shown having a generally trapezoidal shape, it can be appreciated that various other shapes or dimensions may be used.

A sidewall 37 is included in the casing for generally maintaining the sliding member 28 in an initial position. A passage 38 is also defined in the casing 22 which allows movement of the sliding member 28 therethrough. In example embodiments, as shown, the passage 38 is dimensioned to flushly encompass a cross sectional shape of the sliding member 28 (the cross sectional shape shown is defined by the surface area of sidewalls 44b and 44d, which is generally rectangular in this example). The sliding member 28 is movable transversely with respect to the casing opening 36 through the passage 38. When moved, the sliding member 28 and the bottom cover 26 traverse across each other's respective openings 34 and 36 to remove excess sample from the casing opening 36. When the sliding member 28 is moved, a ridge 40 of the bottom cover 26 flushly engages the sidewall 44a-44d of sliding member 28 to accomplish this. Once the excess sample is removed, the remaining sample is retained within the casing opening 36 having the specified volume, with the remaining sample thereby being metered by the cartridge 20. The remaining sample in the casing opening 36 may be used to carrying out the desired testing reaction.

Any excess sample remaining within the sliding member opening 34 may be deposited or disposed into a recess 42 defined within the bottom cover 26. The recess 42 may be sloped, as shown, which has an increasing volume in a direction away from the casing opening 36. In the embodiment shown, this wedge-shaped recess 42 can be referred to as a sample disposing region.

The sample disposing region can be monitored to ensure that enough sample for metering has been applied. Monitoring may be achieved by several methods, for example by optical signal or by supplying the disposing region with reagents that change their chemical or physical characteristics upon interacting with the excess sample in the sample disposing region. According to example embodiments, the sample disposing region is treated with or contains a suitable chemical reagent which reacts with the excess sample to give a visual indication of the presence of excess volume. The visual indicator may be a color change, a pH sensitive material, etc. Reflective monitoring of the reagent may also be used in some embodiments. In some example embodiments, the sample disposing region may be provided with adsorbing material (not shown) to ensure quick removal of excess sample, once the cartridge is actuated.

Figure 3:
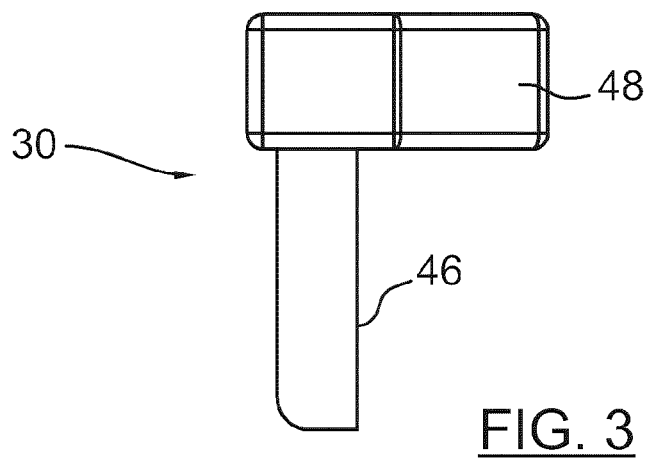
FIG. 3 shows a side view of an example actuation mechanism in accordance with an example embodiment, to be used in the testing cartridge of FIG. 1A.
Figure 4:
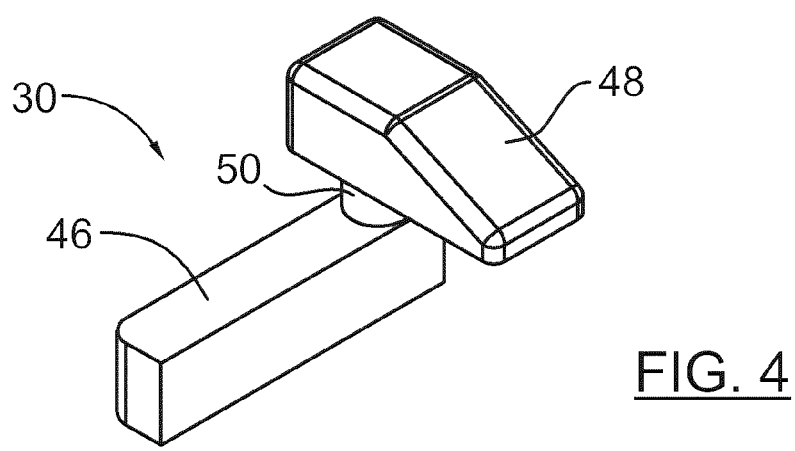
FIG. 4 shows a perspective side view the actuation mechanism of FIG. 3.

Reference is now made to FIGS. 3 and 4, which shows the actuation mechanism 30 in greater detail. The actuation mechanism 30 includes an engaging member 46, a receiving member 48, and a neck 50 connected therebetween. Referring again to FIGS. 1A to 1G, the actuation mechanism 30 may travel along a track 52 defined by the top cover 24, and wherein the actuation mechanism 30 is generally maintained in place using the neck 50. The engaging member 46 is used for engaging the sliding member 28 for the transverse movement of the sliding member 28. For example, the engaging member 46 may be a rigid member which is used for pushing the sliding member 28 along the passage 38. The receiving member 48 is connected to the engaging member 46 via the neck 50 (FIG. 1C). As shown, the receiving member 48 is shaped as a tab or ridge and is used to receive an actuation force for movement of the actuation mechanism 30 along the track 52, thereby moving the sliding member 28 through the passage 38. The receiving member 48 may be formed of various materials (such as plastic or rubber) or include additional contours or protrusions, to assist in increasing friction or ergonomics when receiving the actuation force. As described in further detail below, the actuation force may be provided using manual, automated or semi-automated mechanisms.

In some example embodiments, the port 32 can be fitted with a filtration device (not shown) including a filter (not shown) to filter particulate material from the application sample. The pore size of the filter could be any suitable pore size to remove the desired particulate material. The filter may also be treated (chemically or otherwise) to remove non-particulate material to facilitate the testing of the sample.

Figure 5A:
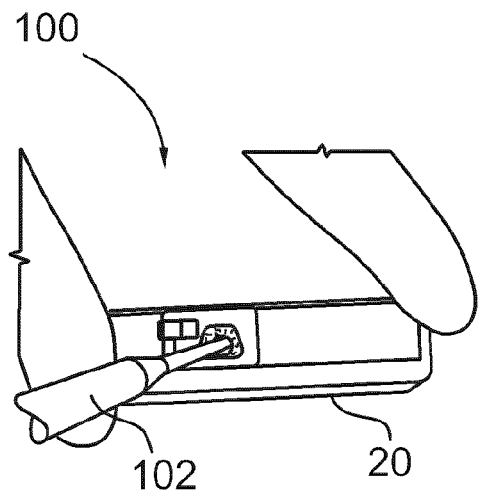
FIG. 5A illustrates an example operation of the testing cartridge of FIG. 1A in an example embodiment.
Figure 5B:
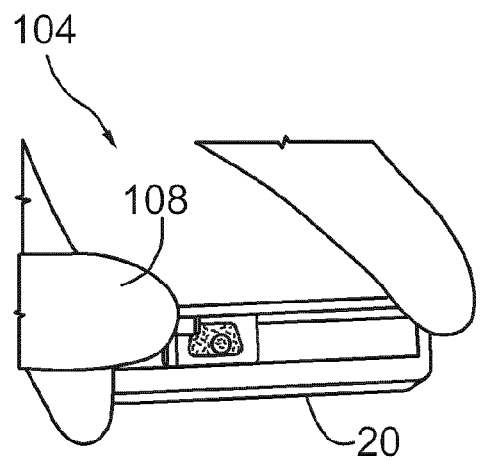
FIG. 5B illustrates an example operation subsequent to FIG. 5A.
Figure 5C:
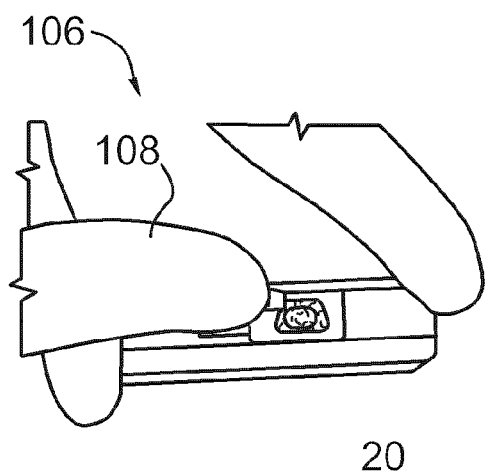
FIG. 5C illustrates an example operation subsequent to FIG. 5B.
Figure 5D:
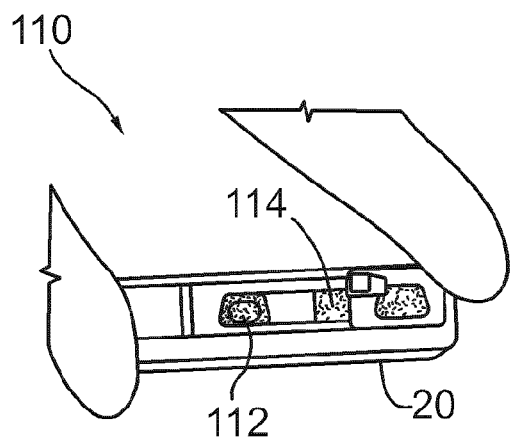
FIG. 5D illustrates an example operation subsequent to FIG. 5C.

Reference is now made to FIGS. 5A to 5D, which illustrates an example manual method of operation of the testing cartridge 20, in accordance with an example embodiment. As shown in FIG. 5A, at process 100 the sample receiving region of the cartridge 20 is filled with the sample using for example a syringe (102) (as shown), or pipette, etc. Typically, the amount of sample inserted exceeds the specified volume defined by the casing opening 36 (described above). In example embodiments, typically relatively few drops of sample are required to be applied to the sample receiving region, and which typically may not need to be premeasured. Next, as represented by process 104 (FIG. 5B) and 106 (FIG. 5C), the receiving member 48 of the actuation mechanism 30 receives a manually pushing force to effect sliding of the sliding member 28. In doing so, the sliding member 28 removes excess sample from the casing opening 36. A thumb (108) (as shown), finger, or other suitable manual tool may be used to provide the actuation force. Referring now to process 110 (FIG. 5D), once the excess sample is removed, the remaining sample 112 is retained within the casing opening 36 and is therefore metered at the specified volume. In some embodiments, the remaining sample 112 in the casing opening 36 may be used to carrying out the desired testing reaction. In other embodiments, the remaining sample 112 is withdrawn using, for example, the syringe 102 to be transported for subsequent processing or testing. Any excess sample 114 remaining within the sliding member opening 34 is deposited or disposed of into the recess 42.

Figure 14A:
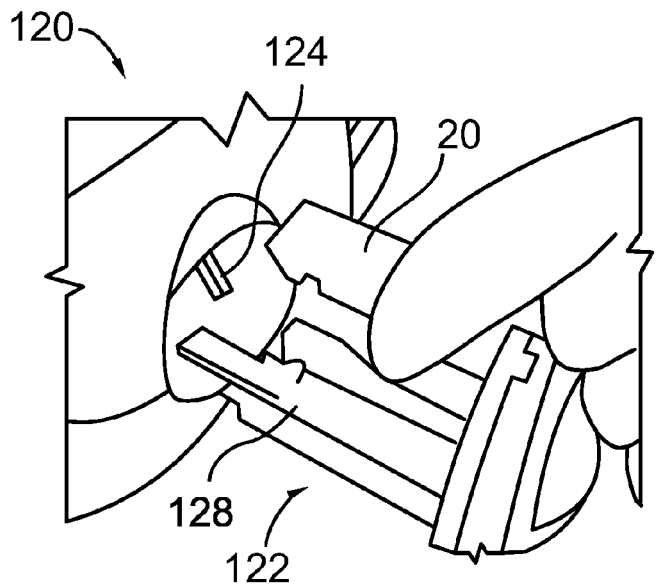
FIG. 14A illustrates a testing system including an instrument for analyzing a testing cartridge in accordance with an example embodiment, and an example operation of the testing cartridge.
Figure 14B:
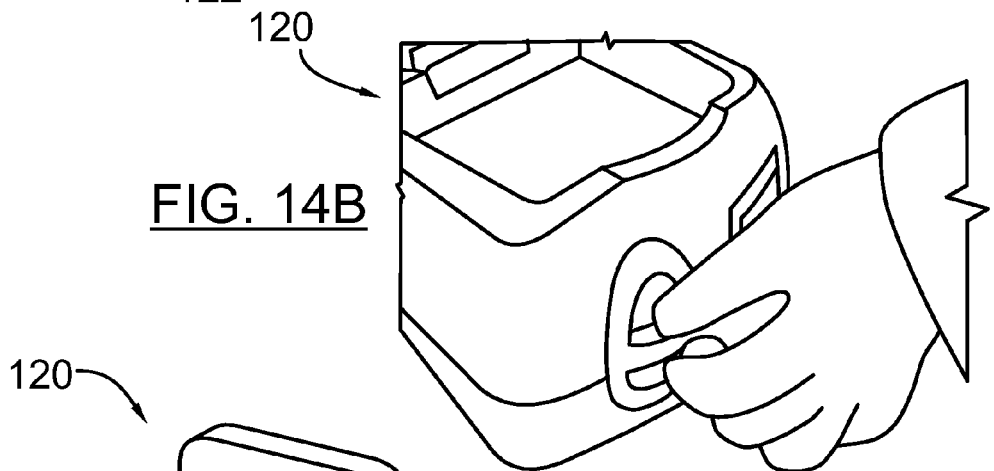
FIG. 14B illustrates an example operation subsequent to FIG. 14A.
Figure 14C:
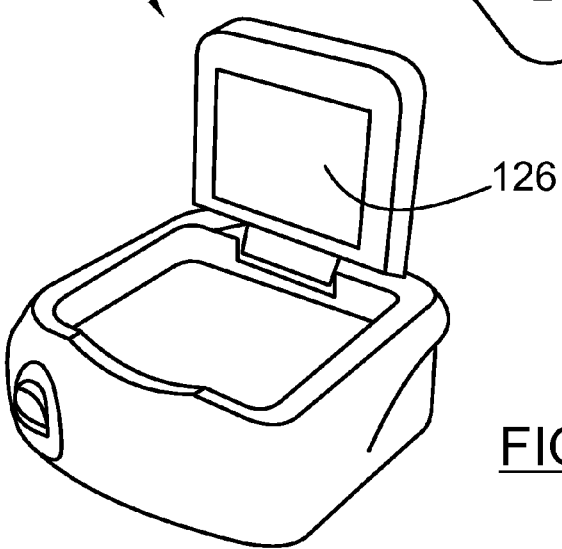
FIG. 14C illustrates an example operation subsequent to FIG. 14B.

Reference is now made to FIGS. 14A to 14C, which illustrates an example automated or semi-automated method of operation of the testing cartridge 20. As shown in FIG. 14C, a testing system 120 may be used to receive the testing cartridge 20, to perform the desired testing reaction on the sample. In various embodiments, the testing system 120 may be used to perform various POC tests which may include blood chemistry such as glucose, lactate, electrolytes, as well as hematology, immunodiagnostics, drugs of abuse, serum cholesterol, fecal occult blood test ("FOBT"), pregnancy, and ovulation. As shown in FIG. 14A, the testing system 120 may include a receiving interface 122 for receiving of the testing cartridge 20, and a rigid flange 124 in the receiving interface 122 which is positioned for engaging the actuation mechanism 30 of testing cartridge 20. The receiving interface 122 may include a cradle 128 for receiving the testing cartridge 20, and can be inserted and retracted from the testing system 120 along a track (not shown). Upon insertion of the cradle 128, the rigid flange 124 acts as an actuation member which engages the actuation mechanism 30 of the testing cartridge 20, thereby pushing the sliding member 28.

In operation, a sample is inserted into the test cartridge 20, which exceeds the specified volume defined by the casing opening 36 (described above). Referring now to FIG. 14A, the testing cartridge 20 is then laid upon the cradle 128. Referring to FIG. 14B, the cradle 128 is inserted into the testing system 120. Upon insertion of the cradle 124 into the testing system 120, the rigid flange 124 pushes the actuation mechanism 30 of the testing cartridge 20, thereby pushing the sliding member 28. Referring now to FIG. 14C, the remaining sample within the casing opening 36 may be used for carrying out the desired testing reaction by the testing cartridge system 120. Applicable results may be displayed on the display screen 126.

In some example embodiments, the testing system 120 includes an existing or off-the-shelf testing system which is retrofitted with the actuation member. In yet further embodiments, the testing system 120 may be fully automated, for example the cradle 128 and other components may be automated without manual intervention. In yet further embodiments, the rigid flange 124 may be configured to move, while the testing cartridge 20 and cradle 128 are fixed in place. It can also be appreciated that other testing cartridges in accordance with example embodiments as described herein may be operated using the testing system 120, and not merely the testing cartridge 20 of FIG. 1A.

Figure 6A:
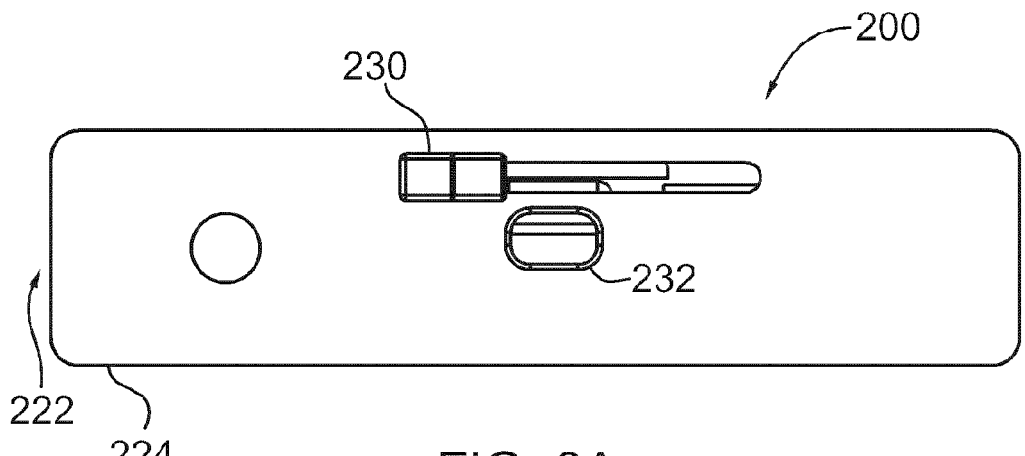
FIG. 6A shows a top view of an example testing cartridge in accordance with a second example embodiment, having a C-shaped sliding member.
Figure 6B:
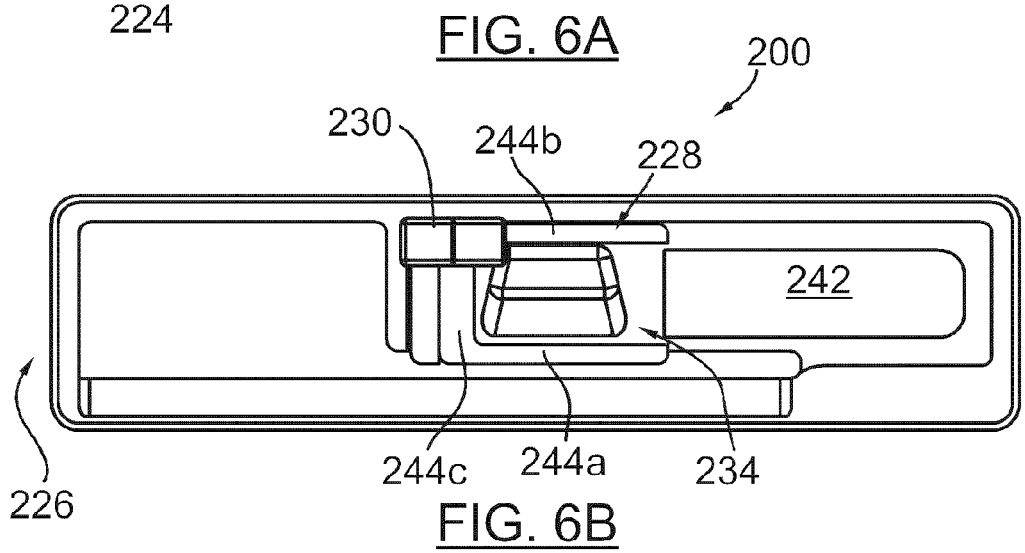
FIG. 6B shows a top view of the testing cartridge of FIG. 6A, shown without a top cover.
Figure 6C:
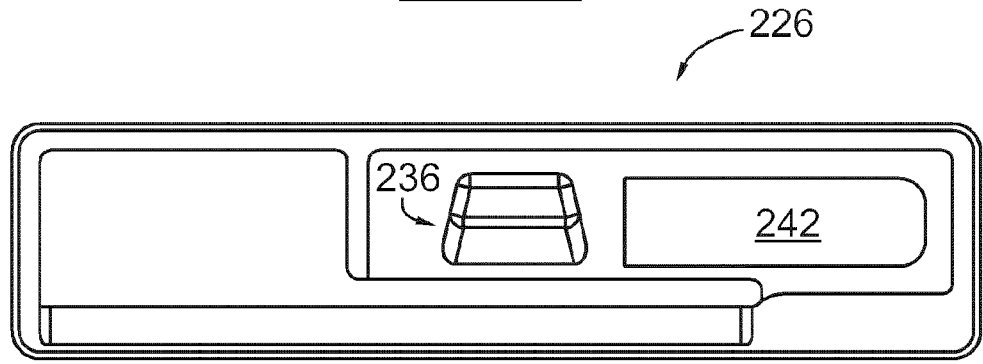
FIG. 6C shows a top view of a bottom cover of the testing cartridge of FIG. 6A.
Figure 7:
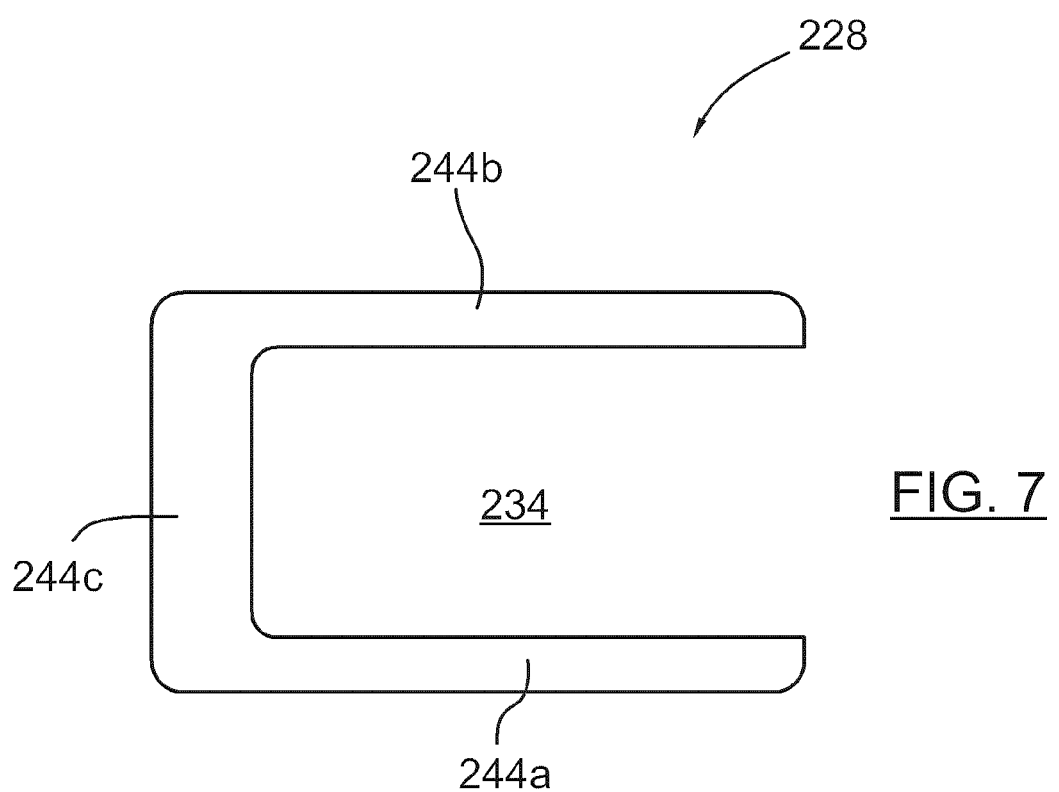
FIG. 7 shows a top view of an example sliding member in accordance with another example embodiment, to be used in the testing cartridge of FIG. 6A.

Reference is now made to FIGS. 6A to 6C, which show another example POC testing cartridge 200 for metering of a sample to be tested, in accordance with another example embodiment. In the embodiment shown, the sliding member opening is defined by one or more open sidewalls, rather than the closed sidewalls as in testing cartridge 20 (FIG. 1A). As best shown in FIG. 7, the sliding member opening 234 is defined by three sidewalls 244a-244c. In the embodiment shown in FIGS. 6A to 6C, the casing 222 includes a top cover 224 and a bottom cover 226 which connect together to collectively generally house the testing cartridge 200. As shown, the testing cartridge 200 also includes a sliding member 228 and an actuation mechanism 230 for moving of the sliding member 228 in a transverse direction.

Referring still to FIGS. 6A to 6C, a sample receiving region may be defined by a port 232, a sliding member opening 234, and a casing opening 236. In such an embodiment, sample may be applied to the casing opening 236 in a manner which may create a meniscus (based on the surface tension) at the casing opening 236 so as to slightly exceed the specified volume of the casing opening 236. When moved, the sliding member 228 and the bottom cover 226 traverse across each other's respective openings 234, 236 to remove excess sample from the casing opening 236. Once the excess sample is removed, the remaining sample is retained within the casing opening 236, with that remaining sample thereby being metered by the cartridge 200. Any excess sample remaining within the sliding member opening 234 is deposited or disposed of into the wedge-shaped recess 242.

In some further example embodiments, the sliding member opening is defined by a single sidewall (not shown). In such an embodiment, sample would be applied to the casing opening in a manner which creates a meniscus (based on the surface tension) at the casing opening so as to slightly exceed the specified volume of the casing opening. The sidewall is positioned to traverse the casing opening to remove excess sample, resulting in the specified volume of sample within the casing opening. In yet further embodiments, the single sidewall may be dimensioned to be an arc, a straight line or a curved ridge.

Figure 8A:
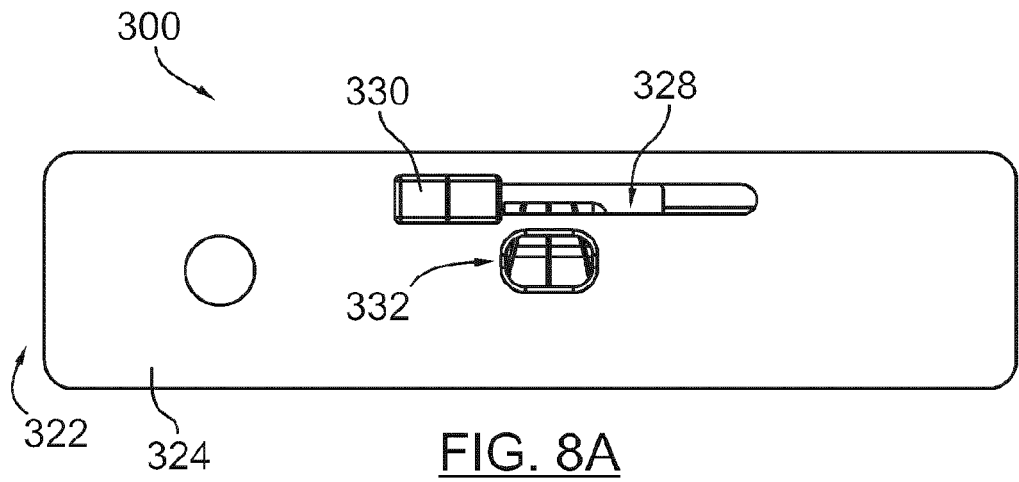
FIG. 8A shows a top view of an example testing cartridge in accordance with a third example embodiment, having multiple wells.
Figure 8B:
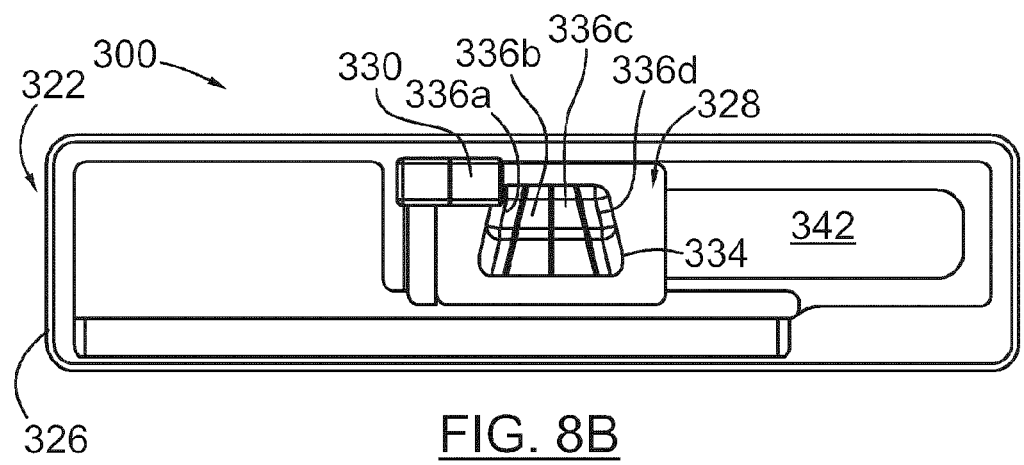
FIG. 8B shows a top view of a top cover of the testing cartridge of FIG. 8A.
Figure 8C:
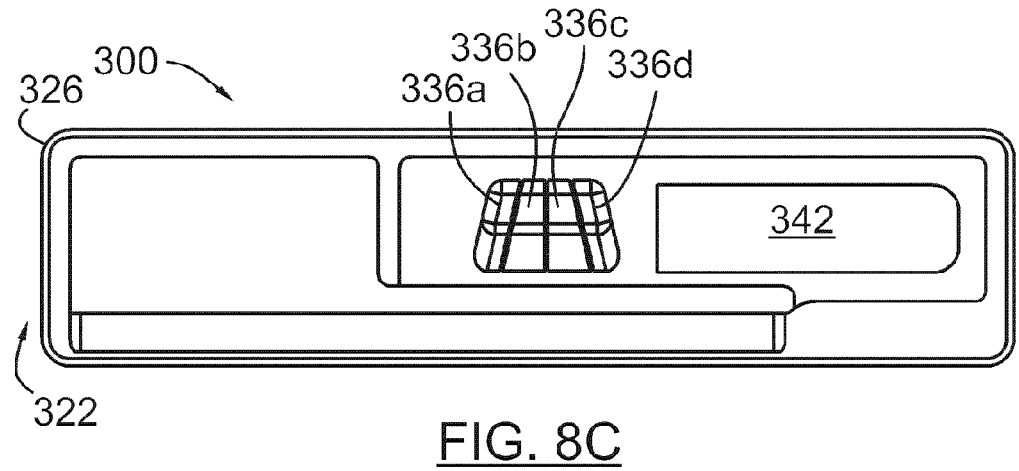
FIG. 8C shows a top view of a bottom cover of the testing cartridge of FIG. 8A.
Figure 9A:
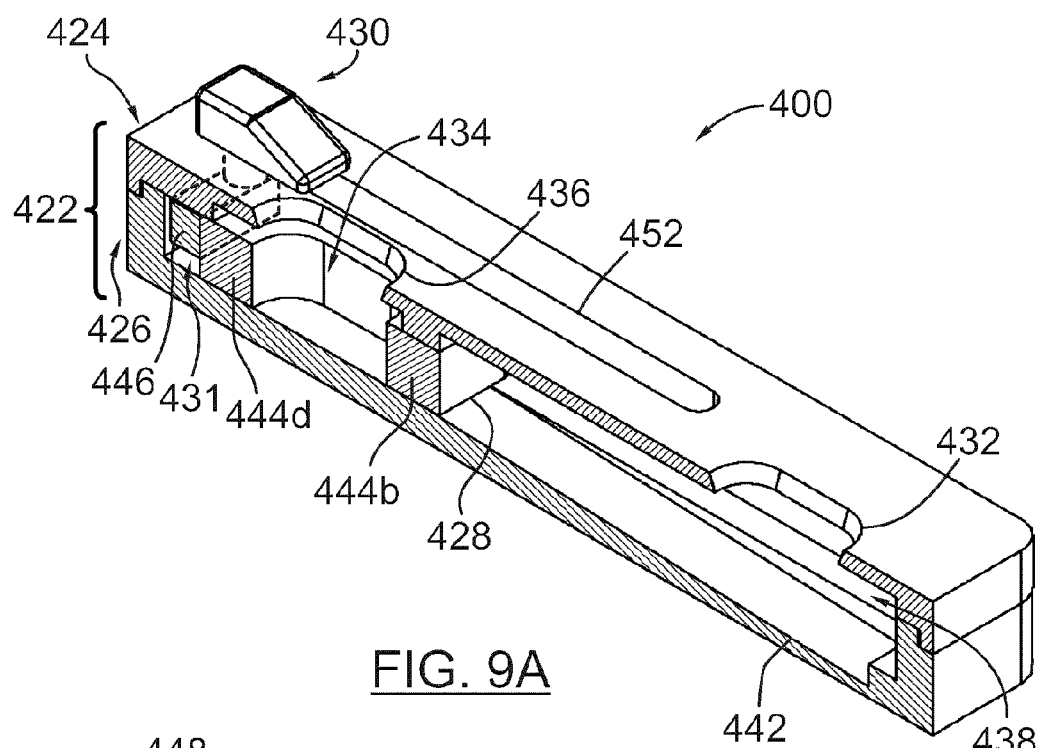
FIG. 9A shows a perspective sectional view of an example testing cartridge in accordance with a fourth example embodiment, wherein a sliding member defines an amount of sample to be tested.
Figure 9B:
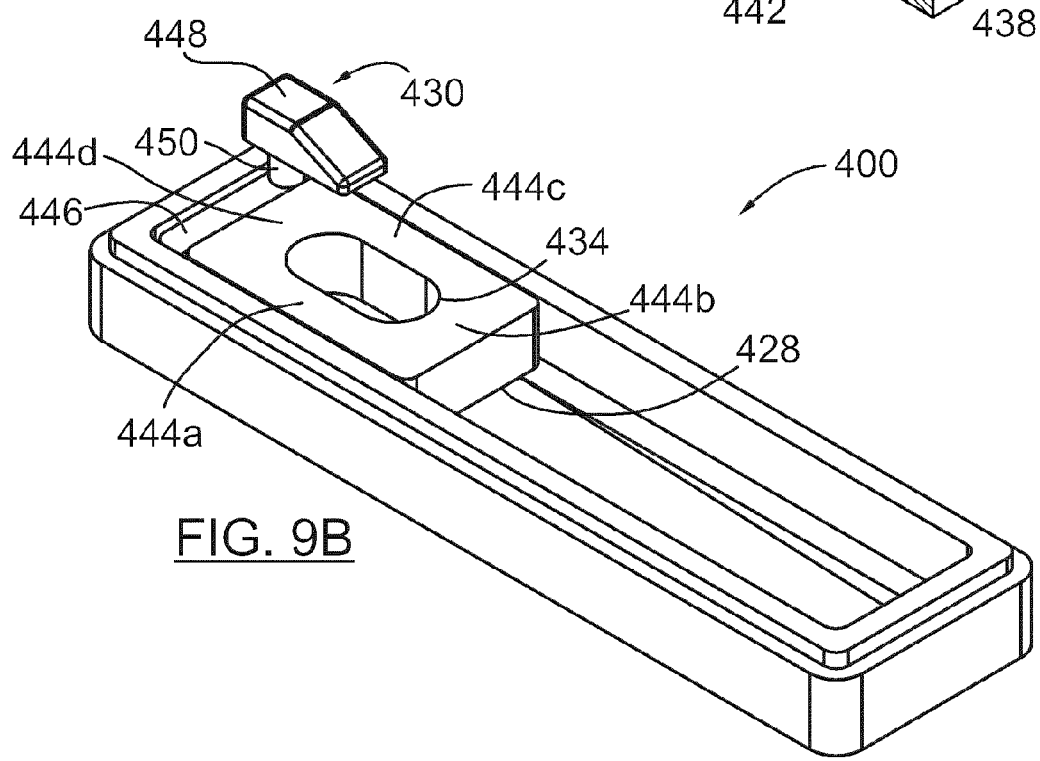
FIG. 9B shows a perspective view of the testing cartridge of FIG. 9A, shown without a top cover.
Figure 9C:
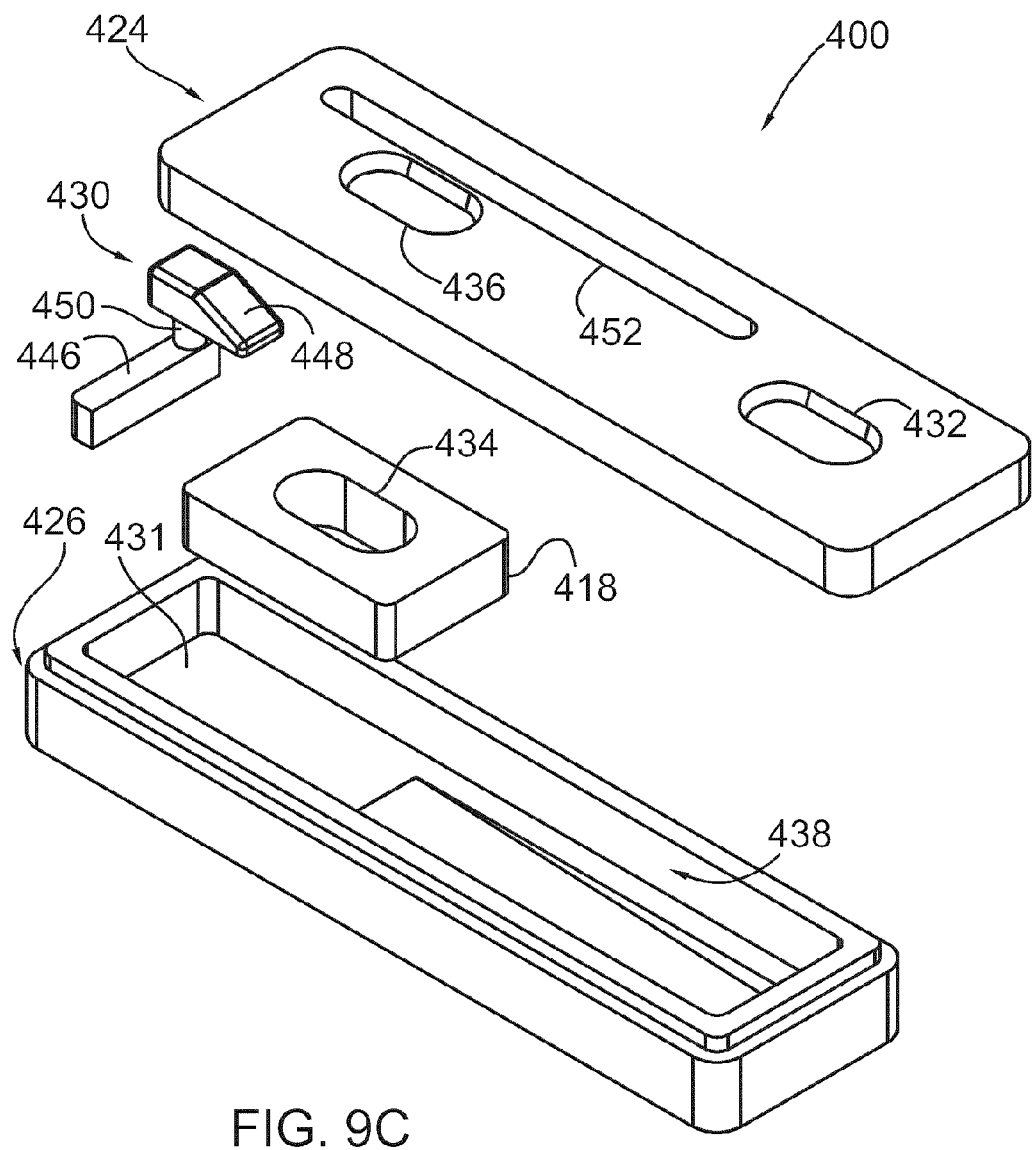
FIG. 9C shows an exploded perspective view of the testing cartridge of FIG. 9A.
Figure 9D:
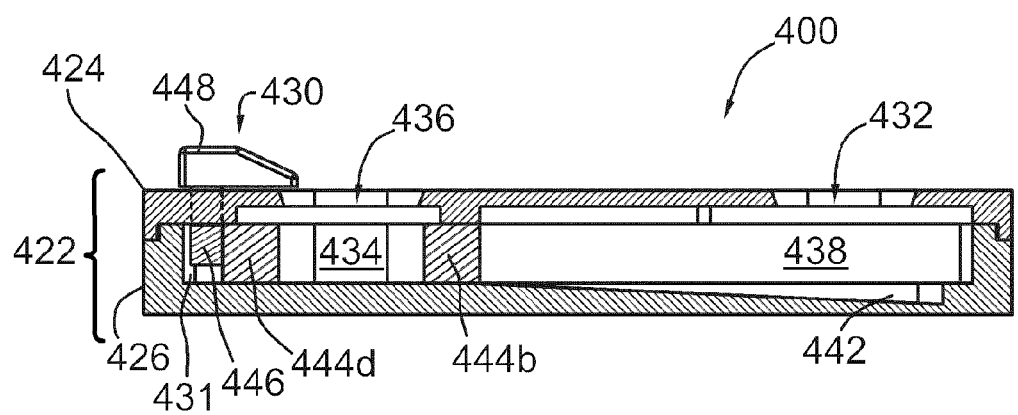
FIG. 9D shows a side sectional view of the testing cartridge of FIG. 9A.
Figure 9E:
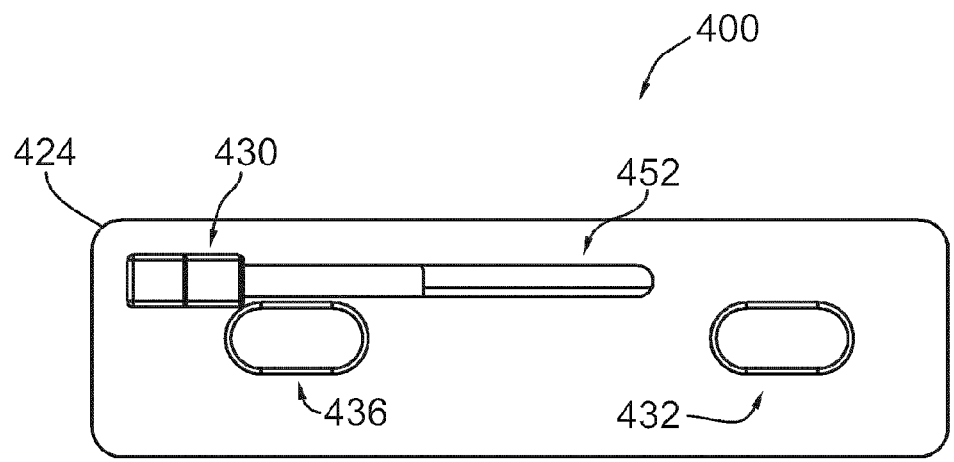
FIG. 9E shows a top view of the testing cartridge of FIG. 9A.
Figure 9F:
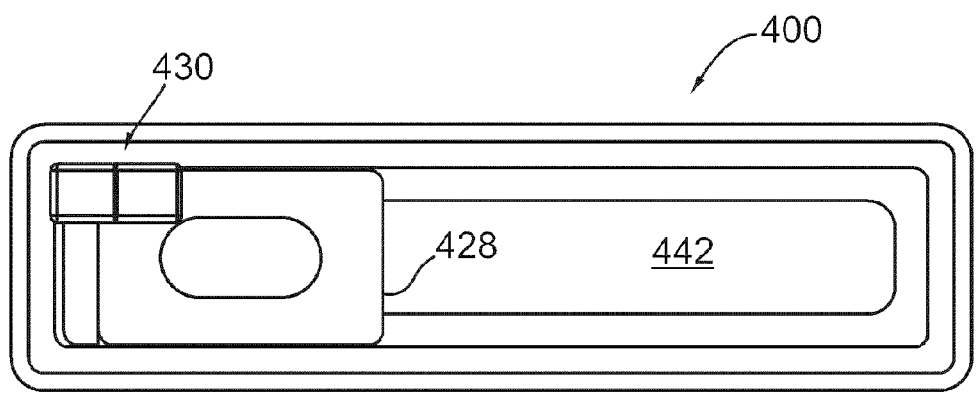
FIG. 9F shows a top view of the testing cartridge of FIG. 9A, shown without the top cover.
Figure 9G:
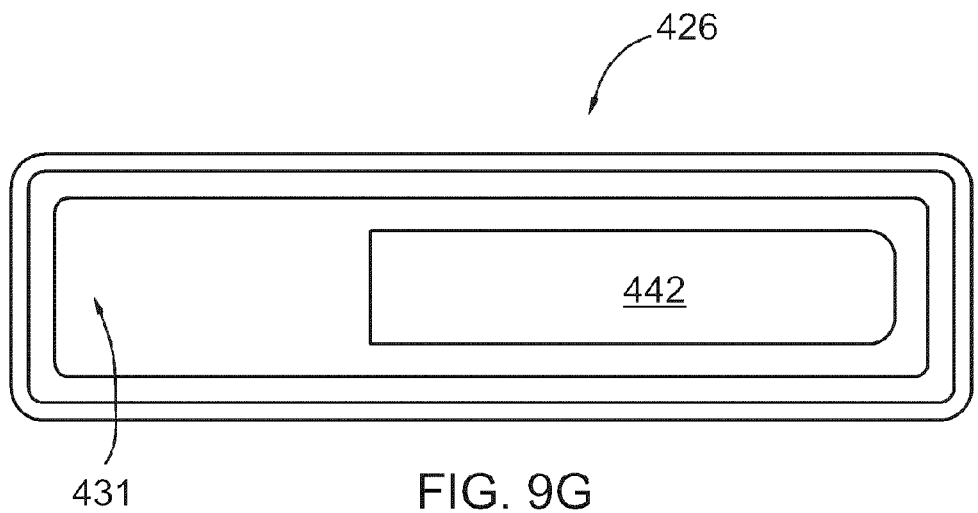
FIG. 9G shows a top view of a bottom cover of the testing cartridge of FIG. 9A.

Reference is now made to FIGS. 8A to 8C, which show another example POC testing cartridge 300 for metering of a sample to be tested, in accordance with another example embodiment. In the embodiment shown, the casing defines a plurality of segregated chambers or compartments, each of the segregated compartments defining an individual chamber volume. In the embodiment shown, the casing 322 includes a top cover 324 and a bottom cover 326 which connect together to collectively generally house the testing cartridge 300. As shown, the testing cartridge 300 also includes a sliding member 328 and an actuation mechanism 330 for moving of the sliding member 328 in a transverse direction.

Referring still to FIGS. 8A to 8C, a sample receiving region may be defined by a port 332, a sliding member opening 334, and casing compartments 336a-336d. The sliding member opening 334 is shown as generally trapezoidal, although it can be appreciated that other shapes and dimensions may be used. As shown, each of the casing compartments 336a-336d define their own specified chamber volume, for providing metering of multiple volumes individually. When moved, the sliding member 328 and the bottom cover 326 traverse across each other's respective openings 334, 336a-336d to remove excess sample from the casing compartments 336a-336d. Once the excess sample is removed, the remaining sample is retained within the casing compartments 336a-336d each having their own specified volume, with the remaining sample thereby being metered by the cartridge 300. The remaining sample within each casing compartment 336a-336d may each or collectively be used to carrying out the desired testing reaction. Any excess sample remaining within the sliding member opening 334 is deposited or disposed of into the wedge-shaped recess 342.

In example embodiments, each of the individual volumes of the casing compartments 336a-336d may include the same or different specified volumes, and may have same or different dimensions. According to some example embodiments, within the cartridge 300 one of the compartments is used or designated for monitoring rather than testing. Various monitoring techniques may be used to detect or confirm that the specified amount of volume has been metered. Further examples of monitoring are described herein, and may for example include a reagent which provides an indicator.

Reference is now made to FIGS. 9A to 9G, which show an example POC testing cartridge 400 for metering of a sample to be tested, in accordance with an example embodiment. In the embodiment shown, the testing cartridge 400 generally includes a sliding member 428 which defines an amount of sample to be tested. The testing cartridge include a casing 422 having a top cover 424 and a bottom cover 426 which connect together to collectively generally house the testing cartridge 400. As shown, the testing cartridge 400 includes an actuation mechanism 430 for moving of a sliding member 428 in a transverse direction.

Figure 10:
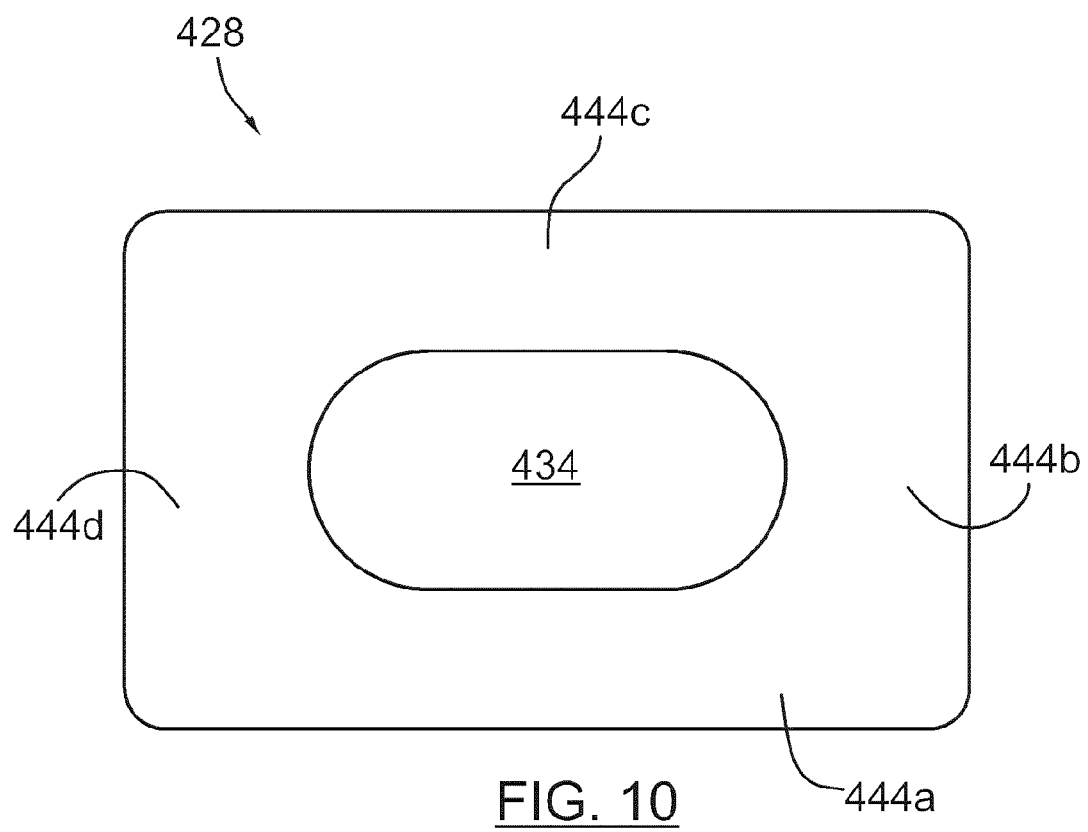
FIG. 10 shows a top view of an example sliding member in accordance with an example embodiment, to be used in the testing cartridge of FIG. 9A.

Referring still to FIGS. 9A to 9G, a sample receiving region may be defined by a casing opening 436 and a sliding member opening 434. For example, a sample to be tested can be applied to the sample receiving region, which can be metered by the cartridge 400 to provide consistently measured volumes in accordance with example embodiments. The casing opening 436 is defined by the top cover 424. Referring briefly to FIG. 10, which shows a top view of the sliding member 428, the sliding member opening 434 is defined by four enclosed sidewalls 444a-444d of the sliding member 428. In the example shown in FIGS. 9A to 9G, the sliding member opening 434 defines a specified volume, which is the desired volume of the sample to be tested. In use, the sample receiving region is dimensioned to accommodate an amount of sample which exceeds the specified volume defined by the sliding member opening 434, wherein the sample may fill at least part of the casing opening 436 as well. Although the sliding member opening 434 and casing opening 436 are shown having a generally oval shape, it can be appreciated that various other shapes or dimensions may be used.

A passage 438 is also defined in the casing 422 which allows movement of the sliding member 428 therethrough. In example embodiments, as shown, the passage 438 is dimensioned to flushly encompass a cross sectional shape of the sliding member 428 (the cross sectional shape shown is defined by the surface area of sidewalls 444b and 444d, which is generally rectangular as shown). The sliding member 428 is movable transversely with respect to the casing opening 436 through the passage 438. When moved, the sliding member 428 and the top cover 424 traverse across each other's respective openings 434, 436 to remove excess sample from the sliding member opening 434. When the sliding member 428 is moved, an edge of the casing opening 436 flushly engages the sidewalls 444a-444d to accomplish this. Once the excess sample is removed, the remaining sample is retained within the sliding member opening 434 having the specified volume, with the remaining sample thereby being metered by the cartridge 400. The remaining sample in the sliding member opening 434 may be used to carrying out the desired testing reaction. A port 432 is also defined by the top cover 424 for introduction of, for example, a syringe or pipette to apply a reagent or other chemical to perform the desired testing reaction within the cartridge 400. In other embodiments, the syringe or pipette may be used to withdraw the now-metered specified volume from the sliding member opening 434.

The excess sample removed from the sliding member opening 434 thereafter spills into a spillover region 431 of the casing 422. In some example embodiments, the spillover region 431 may also contain an adsorbing material (not shown), for adsorbing of the excess sample.

In some example embodiments, the sample remaining within the sliding member opening 434 may be also be deposited into a recess 442 defined within the bottom cover 426. The recess 442 may be sloped, as shown, which has an increasing volume in a direction away from the casing opening 436. Thus, in example embodiments the desired reaction may be performed in the recess 442. In other example embodiments, the recess 442 is pre-treated with or contains a suitable chemical reagent of the desired test.

Reference still to FIGS. 9A to 9G, the actuation mechanism 430 includes an engaging member 446, a receiving member 448, and a neck 450 connected therebetween. The actuation mechanism 430 may travel along a track 452 defined by the top cover 424, and wherein the actuation mechanism 430 is generally maintained in place using the neck 450. The actuation mechanism 430 operates in a similar manner as in the actuation mechanism 30 (FIG. 1A), described above.

Figure 11A:
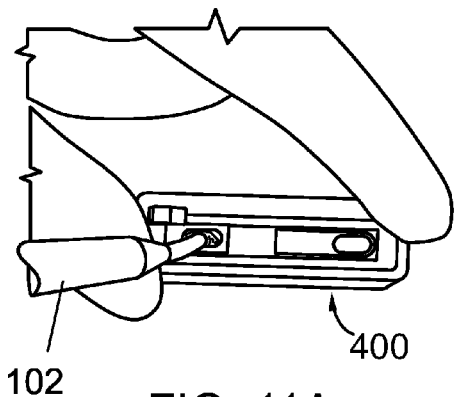
FIG. 11A illustrates an example operation of the testing cartridge of FIG. 9A in an example embodiment.
Figure 11B:
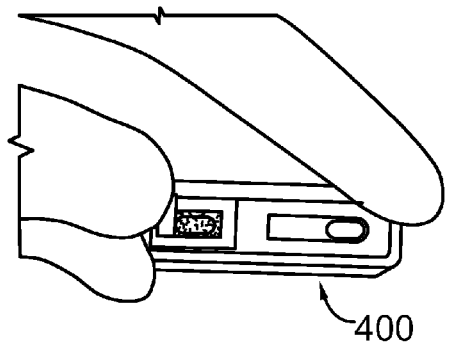
FIG. 11B illustrates an example operation subsequent to FIG. 11A.
Figure 11C:
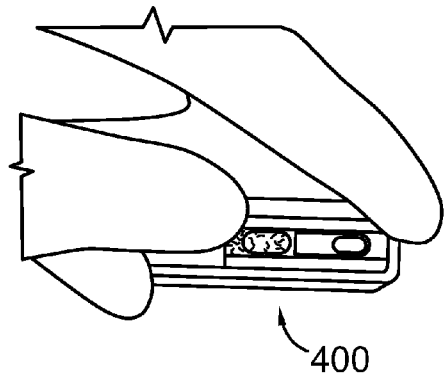
FIG. 11C illustrates an example operation subsequent to FIG. 11B.
Figure 11D:
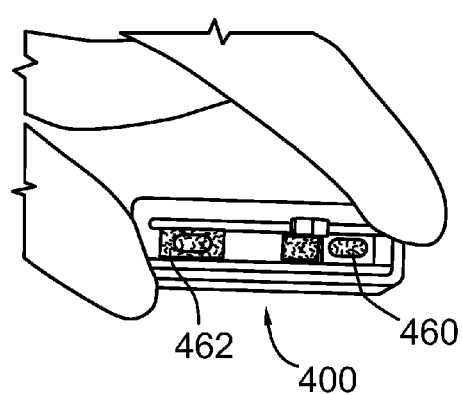
FIG. 11D illustrates an example operation subsequent to FIG. 11C.

Reference is now made to FIGS. 11A to 11D, which illustrates an example manual method of operation of the testing cartridge 400, in accordance with an example embodiment. As shown in FIG. 11A, the sample receiving region of the cartridge 400 is filled with the sample using for example a syringe (102) (as shown), or pipette, etc. Typically, the amount of sample inserted exceeds the specified volume defined by the sliding member opening 434 (described above). Next, as shown in FIG. 11B and FIG. 11C, the receiving member 448 of the actuation mechanism 430 receives a manually pushing force to effect sliding of the sliding member 428. In doing so, the sliding member 428 has excess sample removed therefrom by flush engagement with the top casing 424. A thumb (as shown), finger, or other suitable manual tool may be used to provide the actuation force. Referring now to FIG. 11D, once the excess sample is removed, the remaining sample 460 is retained within the sliding member opening 434 and is thereafter distributed into the recess 442. The remaining sample 460 is therefore metered at the specified volume, which is used to carrying out the desired testing reaction. Any excess sample 462 remaining is deposited or disposed of into the spillover region 431, and in some embodiments may be adsorbed by an adsorbing material (not shown).

Figure 12A:
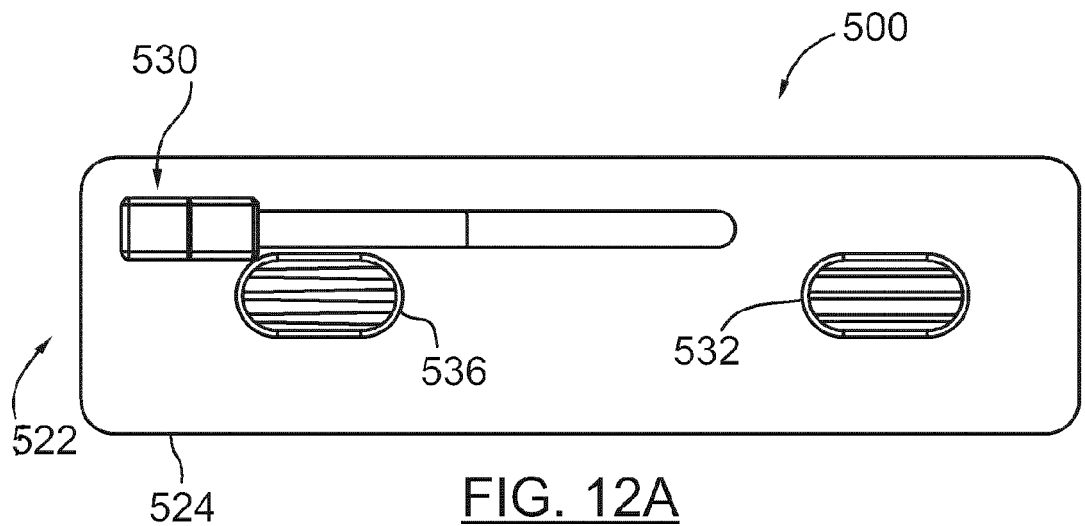
FIG. 12A shows a top view of an example testing cartridge in accordance with a fifth example embodiment, having multiple wells.
Figure 12B:
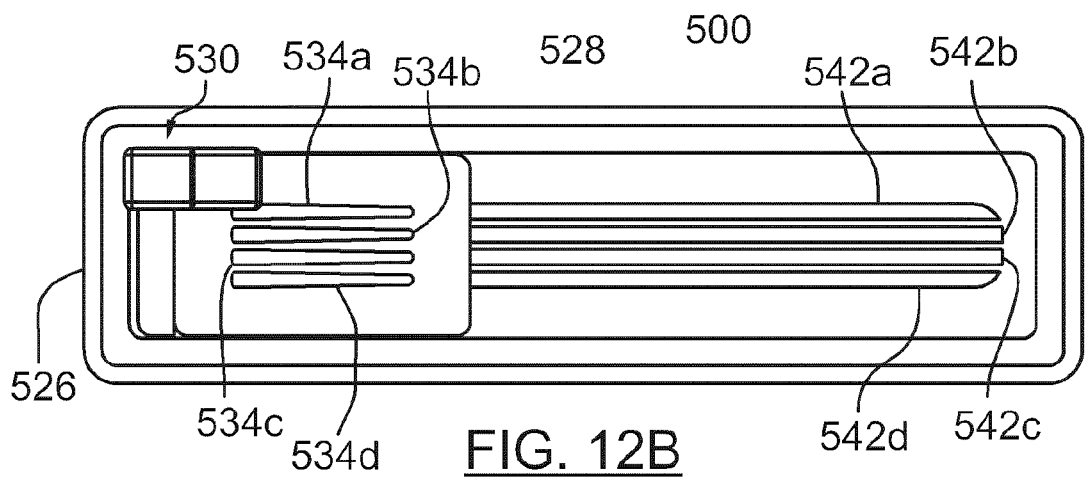
FIG. 12B shows a top view of a top cover of the testing cartridge of FIG. 12A.
Figure 12C:
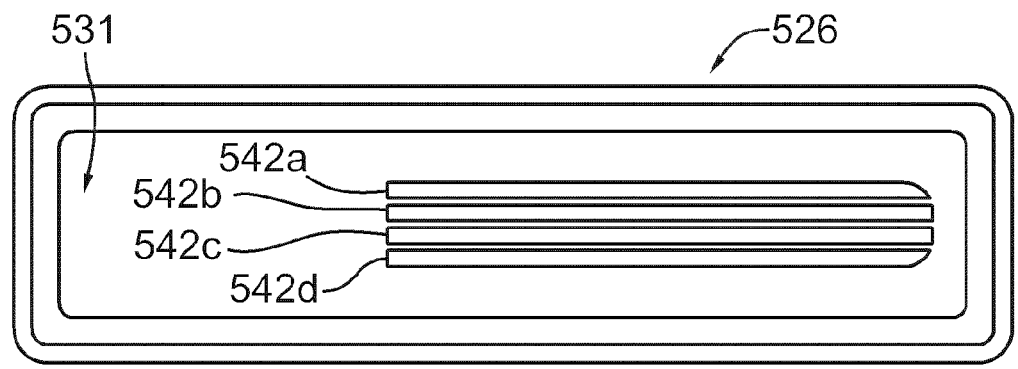
FIG. 12C shows a top view of a bottom cover of the testing cartridge of FIG. 12A.

Reference is now made to FIGS. 12A to 12C, which show another example POC testing cartridge 500 for metering of a sample to be tested, in accordance with another example embodiment. In the embodiment shown, a 522 casing and a sliding member 528 each define a plurality of segregated chambers or compartments, each of the segregated compartments defining an individual chamber volume. In the embodiment shown, the casing 522 includes a top cover 524 and a bottom cover 526 which connect together to collectively generally house the testing cartridge 500. As shown, the testing cartridge 500 also an actuation mechanism 530 for moving of the sliding member 528 in a transverse direction.

Figure 13:
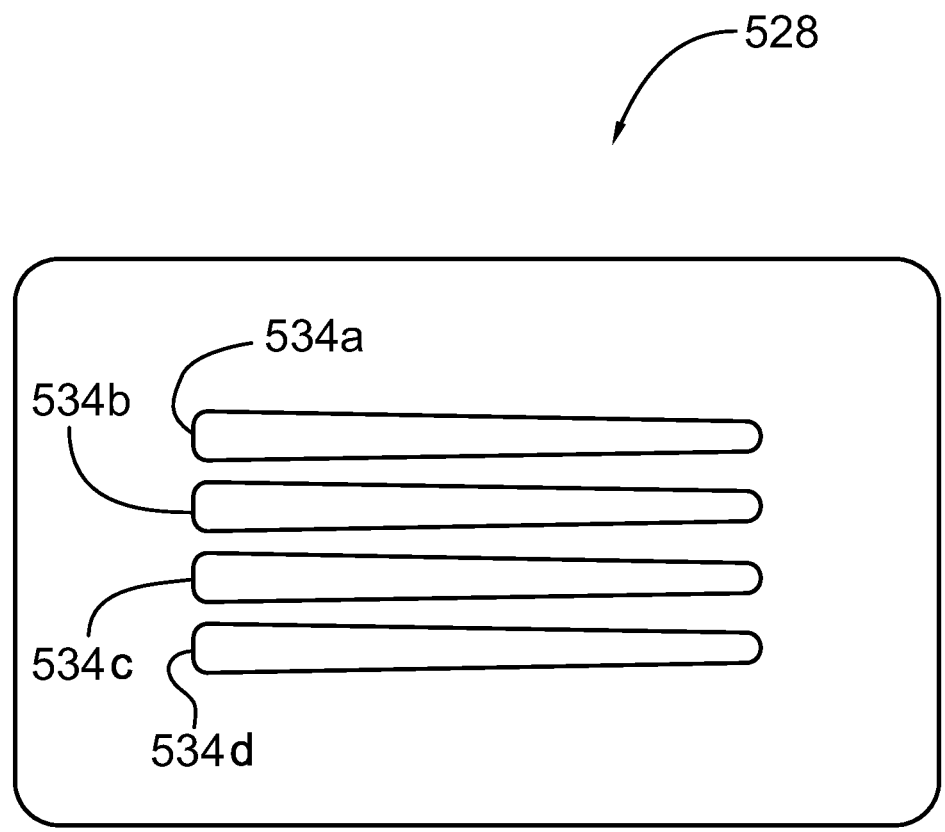
FIG. 13 shows a top view of another example sliding member in accordance with another example embodiment, to be used in the testing cartridge of FIG. 12A.

Referring briefly to FIG. 13, the sliding member 528 may include a plurality of sliding member compartments 534a-534d. Each of the sliding member compartments 534a-534d define their own specified chamber volume, for providing metering of multiple volumes individually. Referring again to FIGS. 12A to 12C, a sample receiving region may be defined by the sliding member compartments 534a-534d, and the casing opening 536. When moved, the sliding member 528 and the top cover 526 traverse across each other's respective openings 534a-534d, 536 to remove excess sample from the sliding member compartments 534a-534d. Once the excess sample is removed, the remaining sample is retained within the sliding member compartments 534a-534d each having their own specified volume, with the remaining sample thereby being metered by the cartridge 500. The remaining sample within each sliding member compartment 534a-534d may each or collectively be used to carrying out the desired testing reaction. In example embodiments, the casing may further define a plurality of individually defined wedge-shaped recesses 542a-542d, each corresponding to one of the sliding member compartment 534a-534d, respectively. The sample remaining within the sliding member opening 534 can be is deposited or disposed of into the wedge-shaped recesses 542a-542d. A test may be performed via port 532. Any excess sample may be discarded to a spillover region 531, which in some embodiments may contain an adsorbing material.

Current example embodiments may allow an individual to add few drops of the test sample to the testing cartridge without the need for prior measuring. The self-metering functionality in the cartridges employs a design and a single-action actuation process that may permit consistently measured sample metering. For example, testing has shown a coefficient of variation of less that 2-3%.

It can be appreciated in the described testing cartridges of example embodiments, the metering mechanisms may use an actuation mechanism to meter the desired sample volume from unmeasured sample by, for example, as little as two steps which are relatively simple to perform.

As can be appreciated, the above-described various example embodiments of testing cartridges and devices may for example allow the employments of material with different surface properties without prior treatment to convert the surface properties in order to facilitate fluid movements. Further, it can be appreciated that the various openings such as casing openings and sliding member openings of example embodiments are of a large enough dimension to be readily manufactured, and which do not typically require complex processes to create capillary channels and the like.

According to some example embodiments, the described testing cartridges may be manufactured from any suitable support material which provides relatively lower cost volume production. One example support material is polymer material manufactured into the specific design via molding processes. Since the accurate volume delivery mechanism may not depend on the surface tension of the support surface, polymer molded to have surface properties of any characteristics could be employed. Other suitable materials include medical grade materials and stainless steel.

In example embodiments, magnetic beads (not shown) may be placed or pre-positioned inside the specified volume where the desired reaction is to take place. The magnetic beads may be manipulated using magnetic fields of a magnet or an electromagnet for further processing, mixing or separation, as would be understood in the art.

Variations may be made to example embodiments. It can be appreciated that, in some example embodiments, reference to the casing opening may include any opening defined by a member included or located within the casing, whether the member is separately constructed or integral to the casing.

The aforedescribed testing cartridges may include or be part of a testing device. Testing devices may include one or more compartments, channels, chambers that are required for the testing procedure and final purpose of the testing cartridge. The testing device may have windows for optical detection, reaction media where the metered sample is required for testing, monitoring windows to ensure the accurate volumes in each of the cartridge compartments, reagents reservoirs where the reagents required for testing are stored in either liquid or dried formats, washing or sample dilution reservoirs, electrodes for electrochemical testing or many other ancillary components required for the specific testing procedure.

According to some example embodiments, the testing device sole is used for accurate metering of an applied non-metered sample as a step in a testing process, the metered sample is then transported to a testing cartridge.

According to some example embodiments, the metering function is a portion of other testing functions supported by the cartridge for particular testing.

In example embodiments, the cartridge includes an assay for sample testing.

In example embodiments, various ancillary elements and compartments can be incorporated in the cartridge to monitor the accurate delivery of a metered sample and also to accommodate any other required functionality.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

What is claimed is:

1. A testing system, comprising:
    a testing cartridge including a casing defining a casing opening, and a sliding member defining a sliding member opening, the casing opening or the sliding member opening defining a specified volume, the casing opening and the sliding member opening collectively defining a sample application region dimensioned to accommodate receiving an amount of sample exceeding the specified volume, wherein the sliding member is movable transversely to the casing opening by having the sliding member and the casing traverse across each other's respective openings to remove excess sample from the received amount of sample and retain the specified volume from the received amount of sample, wherein the testing cartridge further includes an actuation mechanism, wherein the actuation mechanism includes an engaging member for engaging the sliding member for the transverse movement of the sliding member and a receiving member for receiving an actuation force for movement of the actuation mechanism;
    a receiving interface for receiving of the testing cartridge; and
    a second actuation member in the receiving interface for engaging the receiving member of the actuation mechanism for moving of the sliding member.

2. The testing system as claimed in claim 1, wherein the sliding member is contained within the casing and wherein the casing defines a passage for the transverse movement of the sliding member through the passage of the casing.

3. The testing system as claimed in claim 1, wherein the passage is dimensioned to flushly encompass a cross sectional shape of the sliding member.

4. The testing system as claimed in claim 1, wherein the sliding member opening is defined by enclosed sidewalls of the sliding member.

5. The testing system as claimed in claim 1, wherein either the casing opening or the sliding member opening defines the specified volume and is defined by one or more open sidewalls of said casing or sliding member.

6. The testing system as claimed in claim 1, wherein the casing further defines a recess for depositing of sample from the sliding member upon the transverse movement of the sliding member from the casing opening.

7. The testing system as claimed in claim 6, wherein the recess for depositing of sample includes a sloped region being defined separate from the casing opening.

8. The testing system as claimed in claim 1, wherein the specified volume is defined by a plurality of segregated compartments, each of the segregated compartments defining an individual compartment volume.

9. The testing system as claimed in claim 1, wherein the testing cartridge includes a point of care testing cartridge.

* * * * *